United States Patent [19]

Shum et al.

[11] Patent Number: 5,495,052
[45] Date of Patent: Feb. 27, 1996

[54] PROCESS FOR PRODUCING ENANTIOMERICALLY ENRICHED GUAIFENESIN

[75] Inventors: Wilfred P. Shum, West Chester; Harry Mazurek, Bala Cynwyd; Jian Chen, West Chester, all of Pa.

[73] Assignee: Arco Chemical Technology, L.P., Greenville, Del.

[21] Appl. No.: 314,843

[22] Filed: Sep. 29, 1994

[51] Int. Cl.$^6$ .......................... C07C 41/03; C07C 43/205
[52] U.S. Cl. ............................................ 568/648
[58] Field of Search ............................................. 568/648

[56] References Cited

U.S. PATENT DOCUMENTS 4,390,732  6/1983  Merk et al. ............................. 568/648

FOREIGN PATENT DOCUMENTS 139710  12/1950  Australia ............................. 560/648
628497   8/1949  United Kingdom ................ 568/648

OTHER PUBLICATIONS

Nelson et al., "J. Org. Chem.", vol. 42, No. 6, 1977, pp. 1006–1012.

Lopez Calhorra et al., "Chem. Abstracts", vol. 107, 1987, pp. 584, and 585, 23070q.

*Primary Examiner*—Joseph E. Evans
*Attorney, Agent, or Firm*—Stephen D. Harper

[57] ABSTRACT

A tertiary amine is used to catalize the stereospecific ring-opening of chiral glycidol with o-methoxyphenol to afford high yields of enantiomerically enriched guaifenesin. The optical purity of the product may be even further enhanced by recrystallization.

14 Claims, No Drawings

_PROCESS FOR PRODUCING ENANTIOMERICALLY ENRICHED GUAIFENESIN_

FIELD OF THE INVENTION

This invention relates to methods for synthesizing optically active guaifenesin from chiral glycidol using tertiary amine as catalyst. The optically active guaifenesin so obtained may readily be further enriched in the predominate enantiomer by recrystallization.

BACKGROUND OF THE INVENTION

Racemic guaifenesin (also referred to as 3-(2-methoxyphenoxy)-1,2-propanediol) has been known for some time to be clinically effective as an antitussive. Guaifenesin is widely used in racemic form as an expectorant in cough remedy formulations. While there have been no published reports about the pharmacological properties of the individual enantiomers of guaifenesin, it has recently been speculated that perhaps one enantiomer may have greater physiological activity or fewer undesired side effects than the other enantiomer. However, any possible interest in using an enantiomerically enriched form of guaifenesin for medicinal purposes would be tempered by the relatively high cost of obtaining guaifenesin of high optical purity using known synthetic techniques. Several reports suggest that the 2R and 2S isomers of guaifenesin could be prepared using (2R)- or (2S)-glycerol-1,2-acetone [see Nelson et al., J. Org. Chem. 42, 1006–1012 (1977); U.S. Pat. No. 5,025, 031 (Preparation 10); ES 544,545 (Chem Abstracts 107:23070 g)]. Such a synthesis, however, involves at least three steps from a readily accessible starting material. Another report [Wang et al., Tetrahedron Letters 34 (14), 2267–2270 (1993)] indicates that a substituted aryl allyl ether may be asymmetrically dihydroxylated to afford enantiomercially enriched guaifenesin. However, the optical purity of the product obtained, as measured by e.e. value, is only 63%. The development of lower cost processes for obtaining highly enantiomerically enriched guaifenesin thus would be highly desirable.

The reaction of racemic glycidol with various phenols to yield aryl-β,γ-dihydroxypropyl ethers is disclosed in British Pat. No. 628,497. According to the publication, the reaction may be catalyzed by either tertiary amines or quaternary ammonium salts. However, as later noted in U.S. Pat. No. 4,390,732, the disadvantage of this reaction is that the yields are not very high. Additionally, according to the patent, if this general reaction is attempted with o-methoxyphenol for the purpose of preparing racemic guaifenesin, the product obtained is colored and has a very low purity. U.S. Pat. No. 4,390,732 instead recommends the use of a catalyst selected from various alkali metal-containing species in a solventless procedure.

We have now unexpectedly discovered that optically active guaifenesin of exceptionally high enantiomeric purity may be produced in excellent yield using enantiomerically enriched glycidol as a reactant and a tertiary amine as catalyst. This result was surprising in view of the warning in U.S. Pat. No. 4,390,732 that the reaction of racemic glycidol and o-methoxyphenol will yield unacceptable results.

SUMMARY OF THE INVENTION

This invention provides a method for produced enantiomerically enriched guaifenesin comprising reacting o-methoxyphenol with enantiomerically enriched glycidol in the presence of a catalytically effective amount of a tertiary amine to form the enantiomerically enriched guaifenesin.

DETAILED DESCRIPTION OF THE INVENTION

The reactants employed in the process of this invention are well-known organic compounds which are readily available from commercial sources or which may be conveniently prepared by established synthetic methods.

The phenol reactant, ortho-methoxyphenol (also known as guaiacol), may be obtained from Berje Inc., Penta Manufacturing Co., and other manufacturers and distributors. Synthetic routes to o-methoxyphenol include the mercuric oxide oxidation of lignin, oxidation of anisole with trifluoroperoxyacetic acid, the reaction of acetovanilline with zinc chloride, and the reaction of the diazonium salt of o-anisidine.

Enantiomerically enriched glycidol, wherein either the R or S enantiomer of glycidol predominates, may be prepared by various methods, including the enzymatic resolution of racemic glycidol and the asymmetric epoxidation of allyl alcohol. The latter synthesis is now practiced commercially by ARCO Chemical Company, which makes available both R and S glycidol having e.e. values greater than 88%.

The reaction of chiral gylcidol with o-methoxyphenol is catalyzed or promoted by the presence of a tertiary amine, which may be any compound wherein three organic substituents are attached to a common nitrogen atom. Such materials are well-known in the art and may be procured from a number of suppliers. Suitable tertiary amines include the class of organic compounds of nitrogen that may be considered as derived from ammonia by replacing all three of the hydrogen atoms of ammonia with hydrocarbon groups and may contain one or more tertiary amine groups. The tertiary amine may be monomeric, oligomeric, or polymeric in form. Examples of tertiary amines useful in the process of this invention include, but are not limited to, trialkylamines (e.g, triethylamine, diazabicyclo [2.2.2] octane, tetramethylethylene diamine), pyridines, dialkylanilines (e.g., N,N-dimethyl aniline), quinolines, and the like. Also suitable for use are ion exchange resins containing tertiary amine groups such as certain of the "Amberlite", "Amberlyst", and "Dowex" resins which are available commercially.

While the amount of tertiary amine is not critical, a concentration should be used which effectively enhances the rate of the ring-opening reaction of the chiral glycidol by the o-methoxyphenol such that the desired enantiomerically enriched guaifenesin is formed in high yield within a practically short period of time (typically, from 0.1 to 24 hours). The optimum quantity of tertiary amine will vary depending upon a number of variables, including temperature, basicity of the tertiary amine, reactant concentrations, and so forth, but typically from 0.5 to 10 mole percent of tertiary amine based on the molar amount of o-methoxy phenol will suffice.

The relative proportions of enantiomerically enriched glycidol and o-methoxy phenol may be varied considerably but preferably the molar ratio of the two reactants is from 2:1 to 1:2. Good results are obtained using approximately equimolar amounts of each.

The reactants and tertiary amine are contacted at a temperature sufficient to achieve a relatively rapid rate of chiral guaifenesin formation while minimizing competing non-selective reactions. Reaction temperatures of from about 50° C. to 150° C. are generally suitable for such purpose.

While the process of this invention may be performed using the reactants in neat form, the reaction may alternatively be carried out in a liquid medium. Suitable solvents include, for example, alcohols, glycols, glycol ethers, aromatic hydrocarbons, halogenated aromatic hydrocarbons, and aryl alkyl ethers. The solvent selected should be non-acidic and inert towards the reactants.

The reaction of the enantiomerically enriched glycidol and the o-methoxy phenol may be conducted in any suitable vessel, preferably one that is closed and capable of adequately mixing and controlling the temperature of the reaction components. Batch, continuous, or semi-continuous reaction techniques may be used to advantage. The order in which the components are combined is not critical; it may be advantageous to either combine all of the components at once or to add one component incrementally to the other component(s).

Once the ring-opening reaction has proceeded to the extent desired, the enantiomerically enriched guaifenesin may be separated from the remainder of the reaction product by any suitable method. As a consequence of the high chemical and stereoselectivity of the instant process, such separation may be readily achieved. One suitable method involves the use of a reaction solvent in which the guaifenesin is highly soluble at the reaction temperature, but poorly soluble at a temperature of 30° C. or less such that the product crystallizes in purified form upon cooling the reaction mixture. Alternatively, a substance which is a non-solvent for the chiral guaifenesin but which dissolves the other components of the reaction mixture may be added to the crude reaction mixture to precipitate the desired product. Yet another method involves removing volatile components of the reaction mixture by distillation or the like to yield crude guaifenesin, which is thereafter recrystallized from an appropriate solvent. The enantiomerically enriched guaifenesin may also be isolated by fractional distillation techniques.

It has unexpectedly been discovered that the optical purity of the enantiomerically enriched guaifenesin obtained by the process of this invention (which is related to the optical purity of the starting glycidol, but which typically is at least 85%) may readily be further enhanced by recrystallization of the initially isolated reaction product from an appropriate solvent. Such enhancement will be realized even where the e.e. value of the initially obtained reaction product is as low as 20%. This result was surprising in view of the fact that it is well-known in the art that the e.e. values of many chiral glycidol derivatives cannot be improved by recrystallization and that, even where recrystallization does tend to enhance optical purity, the recovered yields of purified derivative is often quite low. In some cases, where an initial recrystallization increases the e.e. value to a certain extent, repeated recrystallizations lead to no further increase in optical purity. In contrast, we have now found that recrystallization is capable of affording (R) or (S) guaifenesin which is free of all but trace amounts of the minor isomer (i.e., products having e.e. values greater than 99%). Without wishing to be bound by theory, it is believed that this favorable result is attributable to the absence of excessive solid solution behavior at high enantiomeric purities. Such recrystallization may be accomplished while still recovering overall high yields of guaifenesin. Ethanol and acetone are recrystallization solvents which are particularly well suited for this purpose. Other non-reactive organic solvents in which the guaifenesin is highly soluble at elevated temperatures, but poorly soluble at ambient or subambient at temperatures may also be utilized. Standard recrystallization techniques may utilized.

Typically, the enantiomerically enriched guaifenesin to be purified is redissolved in hot solvent at a concentration such that crystals of more optically pure guaifenesin form upon cooling of the solution. The solution may be seeded with enantomerically enriched guaifenesin crystals to encourage crystallization.

The following is a description by way of example of methods of carrying the invention into effect.

EXAMPLE 1

A mixture containing 4g of (R)-glycidol (89% e.e.), 6.9 g of o-methoxy phenol, and 0.27 g of triethylamine was heated at 85°–90° C. for one hour. On addition of 8 g of absolute ethanol and cooling to ambient temperature, 8.8 g of enantiomerically enriched (R)-guaifenesin was obtained (80% isolated yield; 97% e.e. by direct HPLC analysis using a chiral stationary phase). This initial product was recrystallized in 13 g of hot ethanol to yield 7.1 g of purified product having an e.e. value of 99%. Further recrystallization in 10 g hot ethanol yielded 5.9 g enantiomerically enriched (R)-guaifenesin having an e.e. value of 99.8%.

EXAMPLE 2

A mixture containing 2.0 g of (S)-glycidol (89% e.e.), 3.4 g of o-methoxy phenol, 0.27 g of triethylamine, and 10 g of absolute ethanol was refluxed for four hours. Solvent was then removed under vacuum to obtain an initial product which was washed with 5 g of acetone. After collecting by filtration and washing with a small quantity of hexanes, 3.8 g (68% yield) of (S)-guaifenesin (97% e.e.) were obtained.

EXAMPLE 3

Example 2 was repeated, except that (R)-glycidol (89% e.e.) was used and the mixture was refluxed for only three hours. The solvent was removed from the reaction mixture under vacuum and the product thus obtained recrystallized from hot ethanol to yield 4.1 g (R)-guaifenesin (97% e.e.).

COMPARATIVE EXAMPLE 4

This comparative example demonstrates that the use of the alkali metal catalysts proposed in U.S. Pat. No. 4,390,732 leads to poorer yields of enantiomerically enriched guaifenesin that those attainable by practice of the present invention wherein a tertiary amine catalyst is utilized.

A mixture of 2 g of (S)-glycidol (89% e.e.), 3.4 g of 2-methoxy phenol, 0.2 g of sodium methoxide, and 10 g absolute ethanol was refluxed for four hours. The solvent was removed under vacuum to obtain an initial product which when recrystallized from acetone gave only a 50% yield of (S)-guaifenesin (97% e.e.). GC analysis of the reaction mixture indicated that a substantial amount of the (S)-glycidol decomposed, apparently due to the presence of the alkali metal catalyst.

COMPARATIVE EXAMPLE 5

This example illustrate the need for a catalyst to achieve good yields of the desired ring-opened product. A mixture of 2.0 g of (R)-glycidol (89% e.e.), 3.4 g o-methoxyphenol and 10 g of absolute ethanol was heated at reflux for 18 hours. The guaifenesin yield based on LC and GC analysis was only 7%.

We claim:

1. A method for producing enantiomerically enriched guaifenesin comprising reacting o-methoxy phenol with enantiomerically enriched glycidol in the presence of a catalytically effective amount of a tertiary amine to form the enantiomerically enriched guaifenesin.

2. The method of claim 1 wherein said reaction is performed at a temperature of from 50° C. to 150° C.

3. The method of claim 1 wherein the enantiomerically enriched glycidol has an e.e. value of at least 85%.

4. The method of claim 1 wherein the molar ratio of o-methoxy phenol to enantiomerically enriched glycidol is from 2:1 to 1:2.

5. The method of claim 1 wherein the tertiary amine is present in an amount of from 0.5 to 10 mole percent based on the molar amount of o-methoxy phenol.

6. The method of claim 1 wherein the tertiary amine is selected from the group consisting of trialkylamines, pyridines, dialkyl anilines, and quinolines.

7. The method of claim 1 wherein said reaction is performed in the presence of a non-acidic inert solvent.

8. The method of claim 1 comprising an additional step of recrystallizing the enantomerically enriched guaifenesin from a solvent to higher optical purity.

9. The method of claim 8 wherein the solvent is ethanol.

10. A method for producing enantiomerically enriched guaifenesin having an e.e. value of at least 85% comprising reacting o-methoxyphenol with enantiomerically enriched glycidol at a molar ratio of from 2:1 to 1:2 in the presence of from 0.5 to 10 moles of a tertiary amine per mole of o-methoxy phenol at a temperature of from 50° to 150° C. to form the enantiomerically enriched guaifenesin.

11. The method of claim 10 comprising an additional step of recrystallizing the enantiomerically enriched guaifenesin from a solvent to higher optical purity.

12. The method of claim 10 wherein the predominate enantiomer present in the enantiomerically enriched guaifenesin is the S isomer.

13. The method of claim 10 wherein the predominate enantiomer present in the enantiomerically enriched guaifenesin is the R isomer.

14. A method for producing guaifenesin of high optical purity comprising reacting o-methoxy phenol with enantiomerically enriched glycidol in the presence of a tertiary amine to form enantiomerically enriched guaifenesin and recrystallizing the enantiomerically enriched guaifenesin from a solvent to higher optical purity.

* * * * *